United States Patent [19]

Edwards et al.

[11] Patent Number: 4,762,847

[45] Date of Patent: Aug. 9, 1988

[54] METHOD OF TREATING ACNE

[75] Inventors: Peter J. Edwards, Leatherhead; Carol A. Jeffryes, Isleworth; Fiona M. Swain, Kettering, all of England

[73] Assignee: Beecham Group p.l.c., England

[21] Appl. No.: 914,265

[22] Filed: Oct. 2, 1986

[30] Foreign Application Priority Data

Oct. 4, 1985 [GB] United Kingdom ............... 8524508

[51] Int. Cl.⁴ .............................................. A61K 31/44
[52] U.S. Cl. .................................. 514/336; 514/345; 514/859
[58] Field of Search ..................... 514/345, 336, 859

[56] References Cited

U.S. PATENT DOCUMENTS 4,185,106  1/1980  Dittmar et al. ................... 514/336

Primary Examiner—Leonard Schenkman
Attorney, Agent, or Firm—Jacobs & Jacobs

[57] ABSTRACT

A topical composition for application to skin affected by acne containing from 0.05 to 2% by weight of Octopirox together with a non-irritant topically acceptable carrier. The composition is particularly useful for treating acne vulgaris.

3 Claims, No Drawings

METHOD OF TREATING ACNE COMPOSITION

The present invention relates to a pharmaceutical composition for topical use, which contains a 1-hydroxy-2-pyridone or a salt thereof. In particular, the invention relates to a pharmaceutical composition for the treatment of acne.

U.S. Pat. No. 4,185,106 discloses a class of 1-hydroxy-2-pyridones which are described as being useful as antidandruff agents. It has now surprisingly been discovered that this class of materials is useful for the treatment of acne, which is nowhere mentioned or suggested in the aforementioned U.S. Patent.

Accordingly, the present invention provides a topical composition suitable for application to skin which is affected by acne, comprising from 0.05 to 2% by weight of a compound of formula (I).

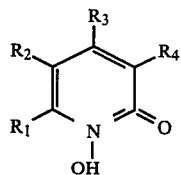
(I)

or a topically acceptable salt thereof in which $R_1$ is hydrogen, alkyl of 1 to 17 carbon atoms, alkenyl of 2 to 17 carbon atoms, cycloakyl of 5 to 8 carbon atoms, bicycloalkyl of 7 to 9 carbon atoms, cycloalkylalkyl of 1 to 4 alkyl carbon atoms, the cycloalkyl groups being optionally substituted by alkyl groups of 1 to 4 carbon atoms, aryl, aralkyl of 1 to 4 alkyl carbon atoms, arylalkenyl of 2 to 4 alkenyl carbon atoms, aryloxy-alkyl or arylthio-alkyl of 1 to 4 alkyl carbon atoms, benzhydryl, phenylsulfonylalkyl of 1 to 4 alkyl carbon atoms, furyl or furylalkenyl of 2 to 4 alkenyl carbon atoms, all the aryl groups mentioned being optionally substituted by alkyl of 1 to 4 carbon atoms, by alkoxy of 1 to 4 carbon atoms, by nitro, cyano or halogen;

$R_2$ is hydrogen, alkyl of 1 to 4 carbon atoms, alkenyl or alkinyl of 2 to 4 carbon atoms, halogen or benzyl;

$R_3$ is hydrogen, alkyl of 1 to 4 carbon atoms or phenyl; and $R_4$ is hydrogen, alkyl of 1 to 4 carbon atoms, alkenyl of 2 to 4 carbon atoms, methoxymethyl, halogen or benzyl, together with a topically acceptable carrier.

Preferred and exemplified compounds of formula (I) are those which are disclosed in the aforementioned U.S. Pat. No. 4,185,106.

A particularly preferred compound of formula (I) is 1-hydroxy-4-methyl-6-(2,4,4-trimethyl pentyl)2(IH)-pyridone ethanolamine salt.

The preferred quantity of the compound of formula (I) or salt thereof in the composition of the invention is from 0.05 to 0.5% by weight, more preferably from 0.2 to 0.5% by weight.

In a further aspect of the invention, there is provided the use of a compound of formula (I), as hereinbefore defined, for the manufacture of a pharmaceutical composition for treating acne in humans, preferably acne in which the organism *Propionibacterium acnes* is implicated.

In a still further aspect of the invention, there is provided a method of treating acne in humans comprising applying a topical composition containing a compound of formula (I) or a salt thereof to the skin of a human suffering from acne.

A particularly preferred use for the composition of the invention is for the treatment of acne vulgaris, which is a polymorphic skin eruption characterised clinically by blackheads, white heads, papules, nodules, cysts and scars occuring particularly on areas of the skin rich in subaceous glands, such as the face, forehead and back.

The topical composition of the invention may be presented in a wide variety of different forms, for example, creams, gels, ointments, lotions, sticks, soaps (liquid or solid), bath additives, shower gels, cleansing pads, impregnated wipes, face packs, shaving foams, aftershaves, atomiser sprays and other conventional cosmetic formulations.

The major requirement in the composition of the invention is that the topically acceptable carrier (which can be any ingredient conventionally used in the above-mentioned compositions) should be non-irritant to an acne sufferer.

Normally, the composition of the invention would be applied two or perhaps three times daily, in accordance with conventional application techniques for topical formulations. The dosage level of active ingredient will depend primarily on whether the composition is a 'leave on' material, such as an ointment, or a 'rinse-off' material, such as a soap. Generally speaking, the dose for a 'rinse-off' formulation would be two or three times that of a 'leave-on' formulation.

Compositions of the invention may be produced by conventional techniques for the manufacture of pharmaceuticals or cosmetics, usually involving admixture of the various ingredients to obtain a uniform composition.

The invention is now illustrated by the following Examples:

EXAMPLE 1

| Gel | w/w percent |
|---|---|
| [1]Octopirox | 0.25 |
| Menthol | 10.00 |
| DEA-oleth-3 phosphate | 2.50 |
| Hydroxypropylcellulose | 2.50 |
| [2]Amphoteric - 1 | 5.00 |
| Water | 39.75 |
| Ethanol (96%) | 40.00 |

[1]Trade Mark of Hoescht for 1-hydroxy-4-methyl-6-(2,4,4-trimethyl pentyl) 2(1H)-pyridone ethanolamine salt.
[2]Amphoteric-1 is the CTFA adopted name for cocoamphoglycinate.

EXAMPLE 2

| Cream | w/w percent |
|---|---|
| [3]Laneth - 10 | 2.00 |
| Lanolin alcohol | 0.50 |
| Cetvl alcohol | 5.50 |
| [4]Polawax | 6.00 |
| Myristyl myristate | 2.00 |
| [1]Octopirox | 0.25 |
| Resorcinol mono-acetate | 0.2 |
| Magnesium aluminium silicate | 4.00 |
| Methyl paraben | 0.20 |
| Sulphur | 1.40 |

-continued

| Cream | w/w percent |
|---|---|
| Perfume | q.s. |
| Water | 77.95 |

[1] Trade Mark of Hoescht for 1-hydroxy-4-methyl-6-(2,4,4-trimethyl pentyl) 2(1H)-pyridone ethanolamine salt.
[2] Amphoteric-1 is the CTFA adopted name for cocoamphoglycinate.
[3] Laneth-10 is the CTFA adopted name for glyceryl lanolate.
[4] Polawax is a Trade Mark of Croda Chemicals Ltd.

Preparation: Dissolve the Octopirox in the propylene glycol and then add the rest of the oil phase ingredients. Add the magnesium aluminium silicate to the water at 75° C. and disperse under shear again to dispense. Combine the phases and emulsify at 70° C., adding the perfume at 50° C.

EXAMPLE 3

| Aerosol shaving cream | | w/w percent |
|---|---|---|
| Part A | Stearic acid | 4.0 |
| | Lauric acid | 2.0 |
| | Liquid lanolin | 1.0 |
| Part B | [1]Cromeen | 3.0 |
| | Triethanolamine | 2.5 |
| | Octopirox | 0.5 |
| | Water (deionized) | 87.0 |
| | Perfume | q.s. |
| | Concentrate | 92.0 |
| | [2]Propellents 12/114 (40:60) | 8.0 |

[1] Cromeen (Croda Chemicals Ltd) is a substituted alkyl amine derivative of various lanolin acids.
[2] Propellent 12 - Dichlorodifluoromethane. (B.P.).
Propellent 114 - Dichlorotetrafluoromethane. (B.P.)

EXAMPLE 4

| Hydrocarbon-propelled aerosol shaving foam | | w/w percent |
|---|---|---|
| Part A | Palmitic acid | 5.0 |
| | Lauric acid | 1.0 |
| Part B | Sodium lauryl sulphate | 1.0 |
| | Polyethylene glycol (400) monolaurate | 0.5 |
| | Polyacrylic acid (40% aq) mol. wt 100 000 | 1.5 |
| | Triethanolamine | 2.0 |
| | Potassium hydroxide | 0.8 |
| | Glycerol | 5.0 |
| | Octopirox | 0.5 |
| | Water (deionized) | 2.8 |
| | Perfume | q.s. |
| | Concentrate | 96.9 |
| | Propellants, isobutane/propane | 3.1 |

Preparation: Heat parts A and B separately to 75° C. Add A to B with vigorous stirring and allow to cool to 35° C., when the perfume is added. The aerosol container is charged when the concentrate has reached room temperature.

EXAMPLE 5

| After shave lotion | w/w percent |
|---|---|
| Octopirox | 0.25 |
| Ethyl alcohol, specially denatured | 60 |
| Propylene glycol | 3 |
| Water, demineralised | 35.75 |
| Perfume | 1 |

Preparation: Dissolve the perfume and propylene glycol in the alcohol and add the water slowly, stirring well to avoid locally high concentrations of water precipitating the less soluble components of the perfume. Allow the solution to stand for several hours at about 4° C., then filter.

EXAMPLE 6

| Bath Liquid | w/w percent |
|---|---|
| Octopirox | 2 |
| Sodium lauryl ether sulphate (28% active) | 50 |
| Coconut diethanolamide | 3 |
| Perfume | 1-2 |
| Citric acid | q.s. to pH 7 |
| Colour, preservative, emollients, solubilizer | q.s. |
| Sodium chloride | q.s. to required viscosity |
| Water | to 100 |

EXAMPLE 7

| Lotion | w/w Percent |
|---|---|
| Octopirox | 0.25 |
| Alcohol | 43.00 |
| Aluminium chlorhydroxyallantoinate | 0.20 |
| Propylene glycol, | 3.00 |
| Menthol | 0.05 |
| Aluminium chlorhydrate (50%) | 5.00 |
| Hydroxypropylmethylcellulose (3%) | 47.75 |
| Mica (and) titanium dioxide | 1.00 |
| Pefume, colour, preservative | q.s. |

EXAMPLE 8

| Stick | w/w percent |
|---|---|
| Sodium stearate | 8.00 |
| Ethyl alcohol | 74.75 |
| Propylene glycol | 10.00 |
| Isopropyl myristate | 5.00 |
| Octopirox | 0.25 |
| Perfume | 2.00 |

Procedure: Slurry the soap in the cold with organic solvents and Octopirox and then heat to 60°-75° C. Stirr the mass while hot until clear. Add fragrance and colour as desired at 5°-8° C. above the set point of the stick. When it is uniform, pour the soap solution into moulds and allow to cool. Sodium stearate can be prepared in situ but critical control is required to avoid excess alkali or fatty acid.

EXAMPLE 9

| Aerosol | w/w percent |
|---|---|
| Octopirox | 0.25 |
| Propylene glycol | 2.00 |

| Aerosol | w/w percent |
|---|---|
| Alcohol (99% v/v) | 57.25 |
| Perfume | 0.50 |
| Propellant 12 | 40.00 |

EXAMPLE 10

| Clear gel face mask | w/w percent |
|---|---|
| Sodium magnesium sililcate | 8.00 |
| PEG - 75 | 1.00 |
| Octopirox | 0.20 |
| Alcohol | 5.00 |
| Carbomer | to pH 7.5 |
| Water | to 100 |
| Perfume, colour, preservative | q.s. |

ANTI-MICROBIAL ACTIVITY

To demonstrate the effectiveness of the preferred compound, Octopirox, of the composition of the present invention, the compound was subjected to in vitro evaluation by agar diffusion against *P. acnes* and *S. aureus*.

METHOD

Octopirox was evaluated at the 0.2% w/v level in either 10% ethanol or 10% *Tween 20. 0.1 ml of each solution was placed in a 1 cm diameter well in Brain Heart Infusion Agar (OXOID) seeded with either *Propionibacterium acnes* (strain 737) or *Staphylococcus aureus* (NCTC 6738).

*Tween is a trade mark of Atlas; Tween 20 is polyoxyethylene sorbitan monolaurate.

The plates containing *Staph. aureus* were incubated aerobically for 24 hours at 37° C. and those seeded with *P. acnes* anaerobically for 48 hours at 37° C.

RESULTS

Zone of Inhibition diameter (mm) (N=2a)

| | P. acnes | | S. aureus | |
|---|---|---|---|---|
| | 10% IMS | 10% Tween | 10% IMS | 10% Tween |
| No antimicro- | NZ | NZ* | NZ | NZ |
| Octopirox | 20.6 | 30 | 19 | 22.7 |

NZ = No zone of inhibition
*Zone of precipitation resulting from extracellular esterase activity.

CONCLUSION

The results demonstrate that Octopirox is effective against the organism *P. acnes* which is associated with the occurence of acne in humans.

ACTIVITY OF OCTOPIROX VS *P. ACNES* IN THE PRESENCE OF AN ARTIFICIAL SEBUM COMPOSITION

METHOD 0.1 ml of the test solutions/suspensions listed below were incorporated into 1 cm wells cut into the surface of 245×245 cm assay plates of brain heart infusion agar seeded with P. Acnes (strain 737) at a level of approx $10^6$ cfu/ml. Zone of inhibition diameters were assessed after 48 hours anaerobic incubation at 37° C.

TEST AGENTS

1. Octopirox (0.2%w/v) in 20% ethanolic solution.
2. As 1 above but also containing 10% artificial sebum.
3. Control—20% ethanol.
4. Control—20% ethanol+10% artificial sebum.

RESULTS

| AGENT | mean zone diameter (mm)(n= 3) | |
|---|---|---|
| | −sebum | +10% sebum |
| Octopirox (0.2%) | 18.2 | 18.7 |
| 20% ethanol | No zone | No zone |
| 20% ethanol + 10% Artificial sebum | No zone | No zone |

CONCLUSION

The results clearly demonstrate the ability of Octopirox to retain activity against *P. acnes* in the presence of an artificial sebum composition.

The artificial sebum used in the above test method has the following composition:

| Ingredient | % w/w |
|---|---|
| Triglyceride Mix (1) | 36 |
| Fatty Acid Mix (2) | 24 |
| Cholesterol | 4 |
| Lanolin | 8 |
| Squalene | 12 |
| Glycerol | 8 |
| Water | to 100% |
| Triglyceride Mix (1) | |
| Glycerol palmitate | 10 g |
| Glycerol oleate | 10 g |
| Fatty Acid Mix (2) | |
| Palmitic Acid | 10 g |
| Oleic Acid | 5 g |
| Myristic Acid | 5 g |

We claim:

1. A method of treating acne in humans comprising applying to the skin of a human suffering from acne a compound of formula (I)

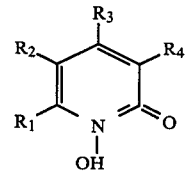

(I)

or a topically acceptable salt in an anti-acne effective amount in which $R_1$ is hydrogen, alkyl of 1 to 17 carbon atoms, alkenyl of 2 to 17 carbon atoms, cycloalkyl of 5 to 8 carbon atoms, bicycloalkyl of 7 to 9 carbon atoms, cycloalkylalkyl of 1 to 4 alkyl carbon atoms, the cycloalkyl groups being optionally substituted by alkyl groups of 1 to 4 carbon atoms, aryl, aralkyl of 1 to 4 alkyl carbon atoms, arylalkenyl of 2 to 4 alkenyl carbon atoms, aryloxy-alkyl or arylthio-alkyl of 1 to 4 alkyl carbon atoms, benzhydryl, phenylsulfonylalkyl of 1 to 4 alkyl carbon atoms, furyl or furylalkenyl of 2 to 4 alkenyl carbon atoms, all the aryl groups mentioned being optionally substituted by alkyl of 1 to 4 carbon atoms, by alkoxy of 1 to 4 carbon atoms, by nitro, cyano or halogen; $R_2$ is hydrogen, alkyl of 1 to 4 carbon atoms, alkenyl or alkinyl of 2 to 4 carbon atoms, halogen or benzyl; $R_3$ is hydrogen, alkyl of 1 to 4 carbon atoms or phenyl; and $R_4$ is hydrogen, alkyl of 1 to 4 carbon atoms, alkenyl of 2 to 4 carbon atoms, methoxymethyl, halogen or benzyl, together with a non-irritant topically acceptable carrier.

2. A method according to claim 1, in which the organism implicated in acne is *Propionibacterium acnes*.

3. A method according to claim 1, in which the human is suffering from acne vulgaris.

* * * * *